United States Patent
Kohlmeier-Beckmann

(10) Patent No.: US 11,952,123 B2
(45) Date of Patent: Apr. 9, 2024

(54) TABLE DEVICE AND PASSENGER SEAT AND VEHICLE CABIN WITH A TABLE DEVICE

(71) Applicant: Airbus Operations GmbH, Hamburg (DE)

(72) Inventor: Carsten Kohlmeier-Beckmann, Hamburg (DE)

(73) Assignee: AIRBUS OPERATIONS GMBH, Hamburg (DE)

( * ) Notice: Subject to any disclaimer, the term of this patent is extended or adjusted under 35 U.S.C. 154(b) by 419 days.

(21) Appl. No.: 17/232,364

(22) Filed: Apr. 16, 2021

(65) Prior Publication Data

US 2021/0323678 A1  Oct. 21, 2021

(30) Foreign Application Priority Data

Apr. 20, 2020 (DE) .......................... 102020110710.2

(51) Int. Cl.
| B64D 11/06 | (2006.01) |
|---|---|
| A61L 2/08 | (2006.01) |
| B64F 5/30 | (2017.01) |

(52) U.S. Cl.
CPC .......... *B64D 11/0638* (2014.12); *A61L 2/088* (2013.01); *B64F 5/30* (2017.01); *A61L 2202/11* (2013.01); *A61L 2202/25* (2013.01)

(58) Field of Classification Search
None
See application file for complete search history.

(56) References Cited

U.S. PATENT DOCUMENTS

| 5,876,262 | A  * | 3/1999  | Kelly ...................... A63H 33/22 |
|---|---|---|---|
|  |  |  | 108/23 |
| 9,302,004 | B2 | 4/2016 | Baumler et al. |
| 10,406,253 | B2 * | 9/2019 | Kreitenberg .............. B64F 5/30 |
| 2007/0200414 | A1 * | 8/2007 | Pozzi ..................... B60N 3/102 |
|  |  |  | 297/217.3 |
| 2008/0047181 | A1 * | 2/2008 | Sakai ...................... G09F 13/04 |
|  |  |  | 40/546 |
| 2016/0041329 | A1 * | 2/2016 | Lin ....................... G02B 6/0055 |
|  |  |  | 362/97.1 |
| 2016/0089459 | A1 * | 3/2016 | Boodaghians ......... B64D 11/00 |
|  |  |  | 250/492.1 |
| 2016/0218257 | A1 * | 7/2016 | Ray ........................... F21S 8/04 |
| 2016/0250362 | A1 * | 9/2016 | Mackin .................. B64D 11/06 |
|  |  |  | 244/118.5 |
| 2018/0236113 | A1 * | 8/2018 | Gross ........................ A61L 2/26 |
| 2018/0339630 | A1 * | 11/2018 | Akaike ............. B64D 11/0638 |
| 2019/0111168 | A1 | 4/2019 | Baumler et al. |

(Continued)

FOREIGN PATENT DOCUMENTS

| DE | 102011012343 A1 | 8/2012 |
|---|---|---|
| EP | 3225112 A1 | 10/2017 |
| EP | 3375774 A1 | 9/2018 |

*Primary Examiner* — David E Allred
(74) *Attorney, Agent, or Firm* — Greer, Burns & Crain, Ltd.

(57) ABSTRACT

A table device for a vehicle cabin, in particular for a passenger cabin of an aircraft. The table device includes an active surface which is coated with at least one active material that is photoactive and antimicrobial. The table device furthermore includes an irradiation device, which is configured to irradiate the active surface with light. A passenger seat or a vehicle cabin may incorporate such a table device.

17 Claims, 3 Drawing Sheets

(56) References Cited

U.S. PATENT DOCUMENTS

| | | | |
|---|---|---|---|
| 2020/0087259 A1 | 3/2020 | Spath et al. | |
| 2020/0281686 A1* | 9/2020 | Finkelstein | A61B 46/20 |
| 2021/0181405 A1* | 6/2021 | Nichol | G02B 6/0016 |
| 2021/0269158 A1* | 9/2021 | Faizan | B64D 11/0638 |
| 2021/0361791 A1* | 11/2021 | Irmen | B64D 11/003 |
| 2022/0219584 A1* | 7/2022 | Ketels | A61L 9/18 |
| 2023/0192299 A1* | 6/2023 | Realyvazquez Guevara | D01F 1/103 |
| | | | 428/352 |

\* cited by examiner

TABLE DEVICE AND PASSENGER SEAT AND VEHICLE CABIN WITH A TABLE DEVICE

CROSS-REFERENCES TO RELATED APPLICATIONS

This application claims the benefit of the German patent application No. 102020110710.2 filed on Apr. 20, 2020, the entire disclosures of which are incorporated herein by way of reference.

FIELD OF THE INVENTION

The invention relates to a table device for a vehicle cabin. The invention furthermore relates to a passenger seat with a table device and to a vehicle cabin with a table device.

BACKGROUND OF THE INVENTION

Hygiene in general, and a low level of microbial pathogens such as bacteria, fungi, protozoa or viruses in interior spaces, or vehicle cabins of vehicles such as aircraft, ships, buses, trains and the like, are of increasing importance. Particularly in passenger cabins which are used by many people in succession, tabletops, for example of folding tables, infant changing tables or the like, are therefore regularly also cleaned in the scope of interior cleaning. It is known that disinfectants, irradiation with UV light or heating of objects to high temperatures can kill microorganisms. However, many surfaces and materials react sensitively to treatment with aggressive cleaning agents, irradiation with UV light or high temperatures. The effectiveness of cleaning of tabletops in passenger cabins in order to disinfect them is therefore limited. Furthermore, such cleaning agents can only be used for cleaning when stopped, or in the absence of passengers, but not during ongoing operation of a vehicle.

Furthermore, the cleaning of folding tables requires them to be put in their usage position and for this purpose folded out. Disinfecting cleaning of tabletops of such folding tables, such as are used, for example, in aircraft cabins or the interior spaces of buses and trains, is therefore time-consuming and laborious.

Antimicrobial substances, for example silver chloride or other compounds comprising silver ions, are furthermore used, for instance to treat drinking water. Photoactive substances which in the scope of a photocatalytic reaction can release oxygen radicals that react with organic compounds and can thereby make microbial pathogens harmless, are furthermore occasionally used in the clinical field. For instance, it is known from DE 10 2011 012 343 A1 to provide medical products, food packaging or hygiene articles which are not thermally stable and by conventional disinfectants, with photosensitized surfaces in order to be able to sterilize them by the action of light. A similar approach is also known from EP 3 225 112 A1 and from EP 3 375 774 A1. In this case, usually either coated products are placed for cleaning purposes in irradiation chambers or under irradiation lamps, or cleaning staff bring a mobile irradiation device to the cleaning location.

SUMMARY OF THE INVENTION

On the basis of the prior art, an object of the present invention is to provide a table device, which allows effective and/or simple disinfection, for a vehicle cabin. It is furthermore an object of the invention to provide a passenger seat and a vehicle cabin having such a table device.

A table device according to the invention for a vehicle cabin, in particular for a passenger cabin of an aircraft, comprises an active surface which is coated with at least one active material that is photoactive and antimicrobial. The table device furthermore comprises an irradiation device which is adapted to irradiate the active surface with light.

The invention furthermore relates to a passenger seat which comprises a table device according to the invention. The passenger seat may comprise a backrest on which the table device is arranged, in particular, rearward. The table device may be adapted to be used by a passenger who is sitting on a further passenger seat that is arranged behind the passenger seat. In other embodiments, the table device may also be fastened on an armrest of the passenger seat and/or on the passenger seat, in such a way that it is adapted for use by the passenger sitting on the passenger seat.

The invention also relates to a vehicle cabin having a table device according to the invention or having a passenger seat according to the invention. The vehicle cabin may be an aircraft cabin, in particular a passenger aircraft cabin, a bus cabin, a ship cabin or a train cabin.

Furthermore, the invention also comprises a vehicle, for example an aircraft, a bus, a train or a ship, having a vehicle cabin according to the invention.

The invention makes it possible to reduce a bioburden of a surface of a table device for a vehicle cabin reliably and effectively. In this way, the hygiene in a vehicle cabin can be improved. In addition, cleaning work may be reduced, for example, because the surface of the table device does not need to be cleaned with disinfectant and/or folded out for cleaning. It furthermore makes it possible to clean the surface of a table device during a flight or a journey, even in the presence of a passenger, so that contagion risks and a duration of cleaning when a vehicle is stopped can be reduced. In this case, it is to be noted that viruses are likewise meant to be understood as microorganisms or germs in the context of this disclosure.

According to one embodiment, the table device is intended to be arranged in an aircraft cabin, a bus cabin, a ship cabin and/or a train cabin, preferably a corresponding passenger cabin. The table device may comprise a tabletop. The active surface may be arranged on an upper side and/or a lower side of the tabletop. An edge of the tabletop may also be part of the active surface. The table device may be an aircraft table device, in particular, a folding aircraft cabin table. The door device may be an integral part of the passenger seat and/or configured at least partially in one piece with a component of the passenger seat. The table device may also be a table module. Furthermore, the table device may be used for another purpose and, for example, be an infant changing device, a serving table device, a non-foldable table device, for instance of a seat compartment, a gaming table or the like.

The active material is adapted, in particular, to produce oxygen radicals from atmospheric oxygen in a photocatalytic reaction as a response to irradiation by the irradiation device. The active material may comprise a monolayer of molecules, which, for example, adhere to the active surface as a result of a sensitizing process. As an alternative, the active material may comprise a material layer which is vapor-deposited, printed, sputtered or suitably applied in another way. The active material may comprise organic and/or inorganic components. For example, the active material may comprise, or be, a photoactive metal oxide, for example titanium oxide (or titanium dioxide) or zinc oxide, in which case, both extensive layers and layers of nanoparticles or microparticles, nanorods, nanotubes and the like may be used. Doped materials may furthermore be used. As an alternative or in addition, organic dyes, metal-complex dyes or other organic molecules or polymers may be used. Preferably, the active material is adapted to absorb and/or make photocatalytically usable light with a wavelength of at least 300 nm, preferably at least 350 nm, and preferably visible light.

The irradiation device may comprise at least one LED, OLED, laser diode, electroluminescent film, incandescent lamp, gas discharge lamp or other suitable lighting means. The irradiation device may furthermore comprise an array of lighting means. The irradiation device is adapted, in particular, to irradiate the active surface permanently and/or continuously. In other embodiments, the irradiation device may also be adapted to emit light pulses.

The irradiation device may comprise at least one light source which is arranged at least partially, and, in particular, fully, in the tabletop.

Uniform irradiation of the active surface, and effective cleaning resulting therefrom, may, in particular, be achieved when the irradiation device comprises at least one two-dimensional light source. An area of the two-dimensional light source may correspond substantially to an area of the active surface.

The two-dimensional light source may comprise a planar light guide. For example, the light source may comprise a light-guide plate and one or more lighting means arranged on the frame of the latter, such as LEDs, OLEDs, laser diodes or the like. For example, the planar light guide may be arranged in the tabletop. As an alternative or in addition, the two-dimensional light source may comprise an array of lighting means and/or a luminous film or the like.

According to one embodiment, the two-dimensional light source may be arranged behind the active surface and irradiate it in the manner of background lighting. This way, a distance between the active surface and the light source may be reduced. Light effects, for example illuminated logos, for instance on a lower side of the tabletop and/or on its edge, or side, or the like, may furthermore be produced without additional components being required.

Furthermore, according to some embodiments the table device may comprise a stowage section, which may, for example, be arranged on a rear side of the backrest of the passenger seat. The tabletop may be movable relative to the stowage section between a stowage position and a usage position. In the stowage position, the upper side of the tabletop, in particular, faces toward the stowage section and/or is accommodated at least partially therein. For example, in the stowage position the upper side of the tabletop faces toward the rear side of the backrest of the passenger seat and/or the lower side of the tabletop faces away from the backrest of the passenger seat.

According to the invention, the irradiation device may be adapted to irradiate the active surface in the stowage position. The irradiation of the active surface may then be carried out while the tabletop is not in use, and, therefore in particular, without being noticed by a passenger. Furthermore, the active surface may in this way be cleaned regularly during a journey or a flight, since the tabletop is usually folded in and out by the passenger several times.

Electronic components may, in particular, be stowed in a space-saving way and simply when the irradiation device comprises at least one light source which is arranged in the stowage section. In particular, the entire irradiation device may be arranged in the stowage section and/or in the backrest of the passenger seat. The tabletop may then be free from electronic components. According to other embodiments, light sources of the irradiation device may also be arranged both in the tabletop and in the stowage section.

A long overall period during which cleaning of the active surface takes place may, in particular, be achieved when the table device furthermore comprises a switching unit which is adapted to automatically activate the irradiation device in the stowage position and/or automatically deactivate it in the usage position. The switching unit may be a button and/or a switch which responds mechanically to movement of the tabletop. As an alternative or in addition, a suitable sensor may be used. The switching unit may, for example, by use of a suitable electric circuit and/or a control unit, be adapted to carry out the activation or deactivation of the irradiation device in the event of movement of the table into the stowage position and/or into the usage position only after a predetermined time, for example after a few seconds or minutes. Particularly for the case of activation, this may therefore take place entirely unnoticed by the passenger, which prevents them from repeatedly moving the table to and fro in order intentionally to cause continual activation and deactivation, or to investigate the functionality of the irradiation device, as a result of which a mechanism and/or electronics of the table device could be excessively stressed.

As an alternative or in addition, the table device may comprise a switch, by means of which a user can activate and/or deactivate the irradiation device. The irradiation device may then, for example, be used as a lamp in the usage position and/or in the stowage position of the table, depending on where light sources of the irradiation device are fitted, in particular on an upper side and/or lower side of the tabletop. The switch may be provided in combination with the switching unit and be used, for example, to overwrite deactivation by the switching unit, i.e., according to some embodiments a passenger may reactivate the initially automatically deactivated irradiation device and/or prevent automatic deactivation thereof.

The table device may furthermore comprise a locking element which is adapted to hold the tabletop in the stowage position. The active surface may, in this case, be arranged at least partially on the locking element. The locking element may, for example, be a pushbutton, a rotating knob, a latch element, a lever, an electrical and/or magnetic switch or the like, by means of which the passenger may enable and/or cause movement of the tabletop. Since the passenger repeatedly touches such a locking element, its surface may also be exposed to germs. By this surface being coated with active material, it may likewise be cleaned effectively. The locking element may, in this case, have a light source of the irradiation device which is arranged in the locking element in order to provide the corresponding irradiation.

The invention furthermore comprises a method for cleaning an active surface, coated with the described active material, of a table device, in particular of a table device according to the invention. The method may comprise irradiation of the active surface with light. If the active surface is arranged on an upper side of a tabletop of the table device and the tabletop can be brought into a stowage position, the irradiation preferably takes place in the stowage position.

BRIEF DESCRIPTION OF THE DRAWINGS

Preferred embodiments of the invention will now be explained in more detail with the aid of the appended schematic drawings, of which

DETAILED DESCRIPTION OF THE PREFERRED EMBODIMENTS

Figure 1:
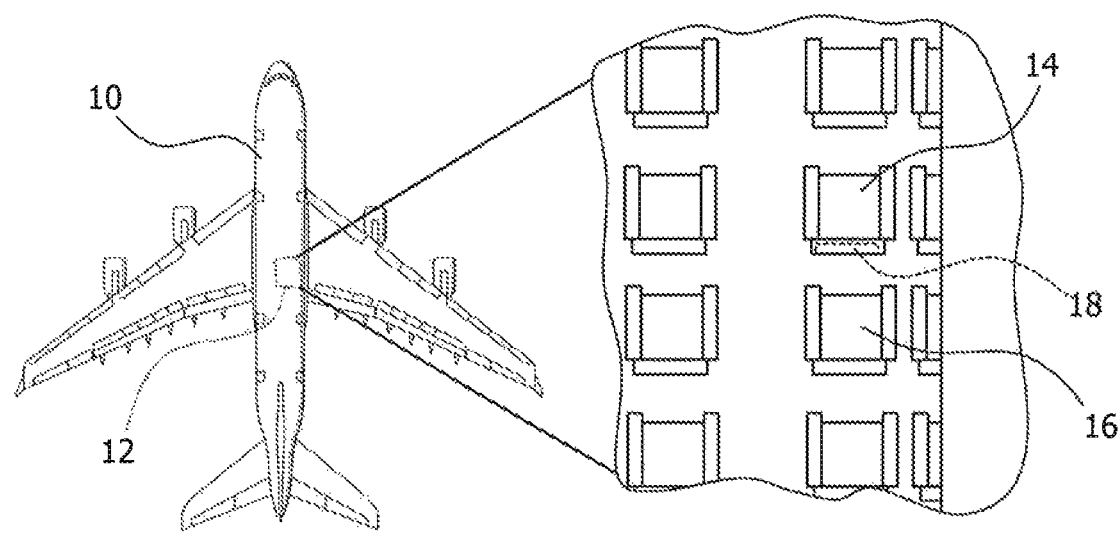
FIG. 1 shows a cabin region of a vehicle cabin with a passenger seat.

FIG. 1 shows an aircraft 10 with a cabin region 12 of a passenger cabin of the aircraft. The invention will be explained below in the context of the aircraft 10. As mentioned above, however, other vehicles may also be envisioned according to the invention.

The cabin region is equipped with a plurality of passenger seats 14, 16, only two of which are provided with references for reasons of clarity. One passenger seat 14 is equipped with a table device 18 on a rear side of its backrest 15. The table device 18 is a folding table device. The table device 18 is adapted to be used by a passenger who is sitting on a passenger seat 16 behind the passenger seat 14 equipped with the table device.

Figure 2:
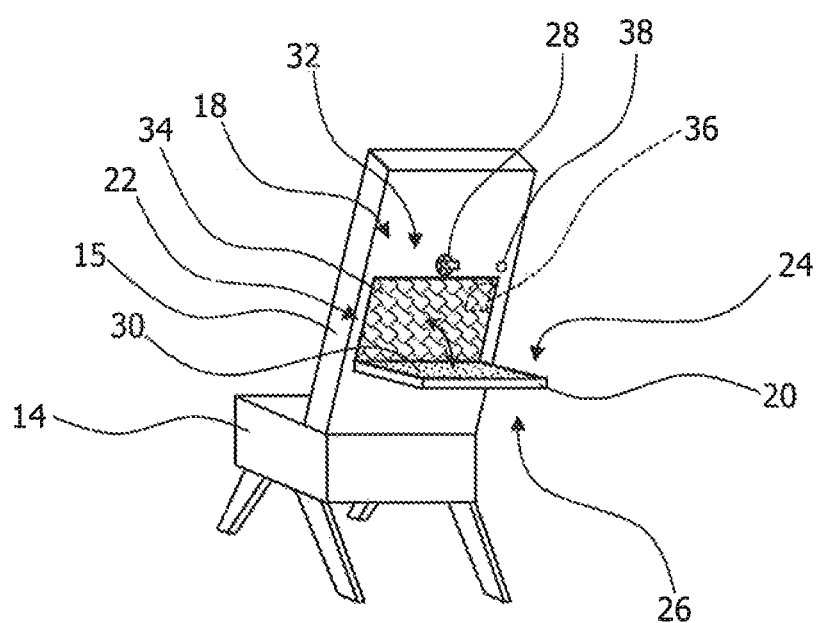
FIG. 2 shows a perspective representation of the passenger seat with a table device.

FIG. 2 shows the passenger seat 14 with the table device 18 in a perspective representation. The table device 18 comprises a tabletop 20 and a stowage section 22, which in the case represented is configured as a two-dimensional stowage compartment. The stowage section 22 is formed in the passenger seat 14, particularly in its backrest 15. The tabletop 20 comprises an upper side 24 and a lower side 26. In the stowage position, the upper side 24 faces toward the stowage section 22 and bears on a rear side of the passenger seat 16, or a rear side of its backrest 15. In the stowage position, the lower side 26 of the tabletop 20 correspondingly faces toward the passenger. The case represented, however, corresponds to a usage position in which the tabletop 20 is folded out so that its upper side 24 can be used to receive and hold objects.

The table device 18 furthermore comprises a locking element 28, which is configured to hold the tabletop 20 in the stowage position. The locking element 28 is, for example, a rotating knob with a holding arm that can be rotated over the lower side 26 of the tabletop 20 when the latter is arranged in the stowage section 22.

Figure 3:
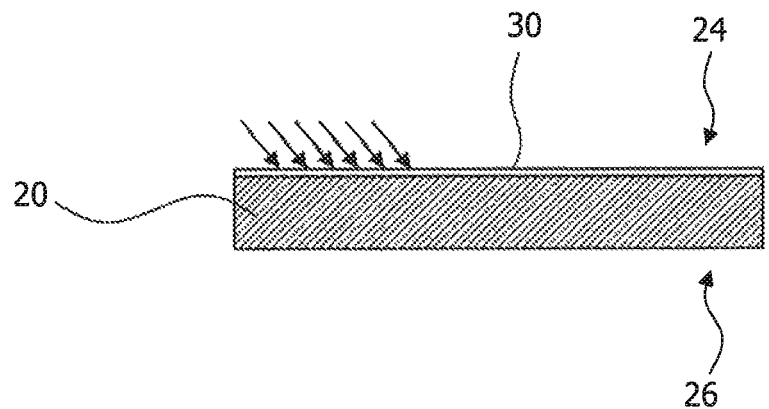
FIG. 3 shows a cross section of a tabletop of the table device.

The table device 18 comprises an active surface 30, which is coated with a photoactive antimicrobial active material. A cross section of the table device 18 is represented in FIG. 3. The active material is configured to produce oxygen radicals from atmospheric oxygen in a photocatalytic reaction as a response to irradiation with visible light and/or with UV light. Germs such as bacteria, viruses or other microorganisms lying on the active surface 30 are attacked by the oxygen radicals produced in this way and are therefore rendered harmless.

The active surface 30 comprises a first region, which is formed on the upper side 24 of the tabletop 20, and a second region which is formed on a surface of the locking element 28. In the case represented, the active surface 30 therefore comprises regions of the table device 18 that are frequently touched by the passenger.

The table device 18 furthermore comprises an irradiation device 32 which is adapted to irradiate the active surface 30 with visible light and/or with UV light. A first light source (not represented) of the irradiation device 32 is arranged in the locking element 28. The locking element 28 is configured to be partially transparent and/or light-guiding, so that the region, arranged on the locking element 28, of the active surface 30 can be irradiated by means of the first light source.

In other embodiments, the locking element 28, its coating with active material and/or the first light source may be omitted.

The irradiation device furthermore comprises a second light source 34, which is configured as a two-dimensional light source. The second light source 34 is arranged in the stowage section 22. In the example represented, the second light source 34 comprises an array of light-emitting diodes or laser diodes which emit light with a suitable wavelength. If the tabletop 20 is in the stowage position, the active surface 30 on the upper side 24 of the tabletop 20 is arranged immediately in front of the second light source 34. The active surface 30 can therefore be irradiated in the stowage position.

For this purpose, the table device 18 comprises a switching unit 36 which is configured to automatically activate the second light source 34 and/or the irradiation device 32 in the stowage position and automatically deactivate it in the usage position. The first light source may likewise be effected by this, so that it illuminates the locking device 28 in the stowage position and is therefore easy for the passenger to find.

Because of the small distance between the irradiation device 32 and the active surface 30, the photocatalytic reaction for germ reduction can therefore take place effectively in the stowage position. The second light source 34 is furthermore automatically deactivated when the passenger wishes to use the tabletop 20.

In the case represented, however, the passenger can activate the irradiation device 32, or the second light source 34, as required. For this purpose, the table device 18 comprises a switch 38 by means of which the automatic deactivation by the switching unit 36 is overridden. The passenger can then use the irradiation device 32 as a lamp in the usage position of the tabletop 20.

Provision may furthermore be made that the passenger can deliberately deactivate the first light source, for example when the light of the locking element 28 is disturbing them.

Figure 4:
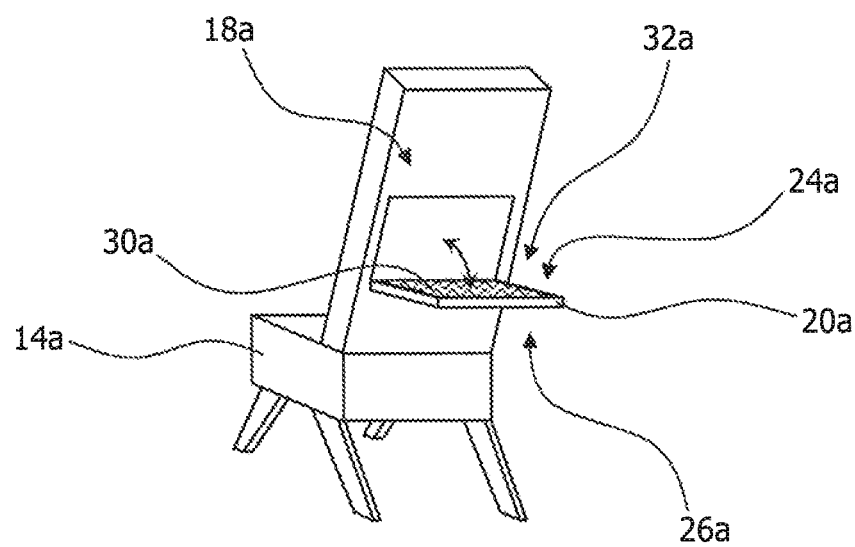
FIG. 4 shows a perspective representation of a passenger seat with a table device according to a further embodiment.

FIG. 4 shows a perspective representation of a passenger seat 14a according to a further embodiment. The passenger seat 14a comprises a table device 18a. The differences from the previous embodiment will primarily be described below. In respect of the function of components that are the same, reference is made to the description above.

Figure 5:
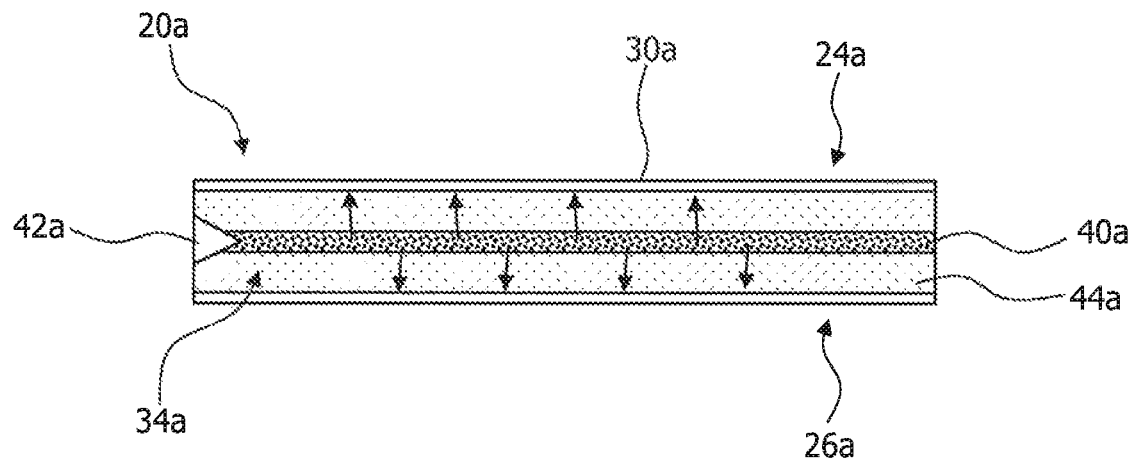
FIG. 5 shows a sectional representation of a tabletop of the table device according to the further embodiment.

The table device 18a comprises a tabletop 20a. FIG. 5 is a sectional representation of the tabletop 20a. The tabletop 20a is coated with active material on its upper side 24a and therefore comprises an active surface 30a. As an alternative or in addition, a coating of active material may also be provided on a lower side 26a of the tabletop 20a.

The table device 18a furthermore comprises an irradiation device 32a having a two-dimensional light source 34a. The two-dimensional light source 34a is arranged in the tabletop 20a. As may be seen in FIG. 5, the light source 34a comprises a planar light guide 40a, which in the case shown is configured as a light-guide plate. Lighting means 42a, which emit into the planar light guide 40a, are arranged along at least one edge of the planar light guide 40a. The lighting means 42a are arranged, for example, in the tabletop 20a.

The two-dimensional light source 34a is arranged behind the active surface 30a and irradiates the active surface 30a in the manner of background lighting. A core 44a, enclosing the two-dimensional light source 34a of the tabletop 20a may correspondingly be transparent in order to transmit and/or guide in a controlled way light emerging from the light source 34a to the active surface 30a. As an alternative, the planar light guide 34a itself may form the tabletop 20a.

In other embodiments, the lighting means 42a can also be arranged in the passenger seat 14 and can be suitably connected optically to the planar light guide 40a. The tabletop 20a may then be configured without electrical components but nevertheless be illuminated from the inside. For example, light may be introducible into the tabletop 20a through hinges and/or through a flexible light-guide section.

Figure 6:
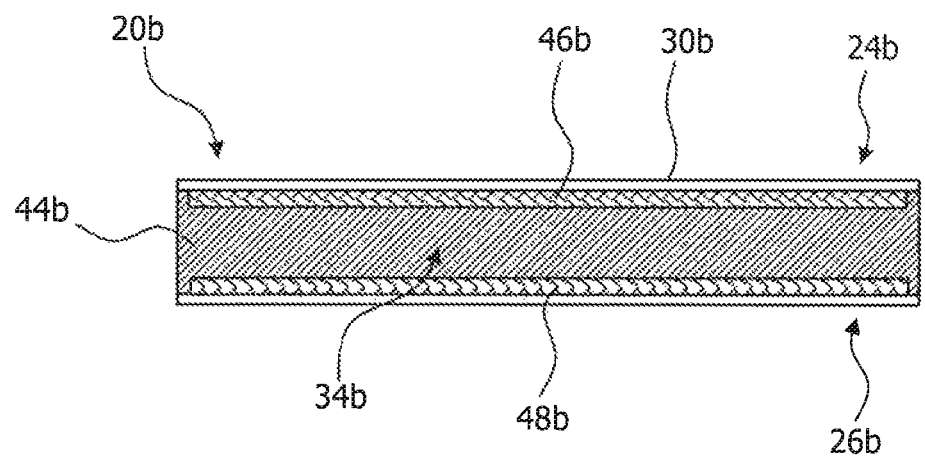
FIG. 6 shows a sectional representation of a tabletop according to yet another embodiment.

FIG. 6 shows a sectional representation of a tabletop 20b according to yet another embodiment. It may, for example, be used in one of the table devices 18, 18a according to the embodiments above. According to this embodiment as well, an irradiation device 32b comprises a two-dimensional light source 34b. The two-dimensional light source 34b comprises an inner-lying illuminated structure, which comprises a transparent core 44b and two two-dimensional lighting means 46b, 48b. The two-dimensional lighting means 46b, 48b may, for example, comprise diode arrays.

By means of the two-dimensional light source 34b, both an upper side 24b and a lower side 26b of the tabletop 20b can be illuminated. In this case, the lower side 26b may be coated with active material. According to other embodiments, only one of the two-dimensional light sources 34b may be provided, for example, in order to irradiate the upper side 24b from behind.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A table device for a vehicle cabin, comprising:
a tabletop having a core located between an upper side and a lower side, the upper side comprising an active surface which is coated with at least one active material that is photoactive and antimicrobial, and the lower side of tabletop also coated with the at least one active material; and
an irradiation device within the core of the tabletop and sandwiched between the upper side and the lower side of the tabletop, the irradiation device configured to simultaneously irradiate the active surface and the lower side of the tabletop with light.

2. The table device according to claim 1, wherein the irradiation device comprises at least one two-dimensional light source.

3. The table device according to claim 2, wherein the two-dimensional light source comprises at least one planar light guide.

4. The table device according to claim 2, wherein the two-dimensional light source is arranged behind the active surface and irradiates the active surface as background lighting.

5. The table device according to claim 1,
wherein the tabletop can be moved relative to a stowage section between a stowage position and a usage position.

6. The table device according to claim 5, wherein the irradiation device is configured to irradiate the active surface in the stowage position.

7. The table device according to claim 6, furthermore comprising a switching unit which is configured to at least one of automatically activate the irradiation device in the stowage position or automatically deactivate the irradiation device in the usage position.

8. The table device according to claim 5, wherein the irradiation device comprises at least one light source which is arranged in the stowage section.

9. The table device according to claim 5,
furthermore comprising a locking element which is configured to hold the tabletop in the stowage position,
wherein the active surface is arranged at least partially on the locking element.

10. The table device according to claim 1, furthermore comprising a switch, by means of which a user can at least one of activate or deactivate the irradiation device.

11. The table device according to claim 1, wherein the active material is configured to produce oxygen radicals from atmospheric oxygen in a photocatalytic reaction as a response to irradiation by the irradiation device.

12. The table device according to claim 1, wherein the vehicle cabin comprises a passenger cabin of an aircraft.

13. A passenger seat, comprising:
a backrest; and
a table device according to claim 1, wherein the table device is arranged on the backrest.

14. A vehicle cabin having a table device according to claim 1.

15. A vehicle cabin according to claim 14, wherein the vehicle cabin comprises an aircraft cabin.

16. A vehicle cabin having a passenger seat according to claim 13.

17. A vehicle cabin according to claim 14, wherein the vehicle cabin comprises an aircraft cabin.

* * * * *